United States Patent [19]

Schumann

[11] Patent Number: Plant 5,938

[45] Date of Patent: Apr. 14, 1987

[54] GERANIUM PLANT NAMED CASINO

[75] Inventor: Ingeborg Schumann, Bad Ems, Fed. Rep. of Germany

[73] Assignee: Fischer Geraniums, Inc., Netherlands Antilles

[21] Appl. No.: 761,097

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Casino having a dark salmon flower color with a white under surface; semi-double flower form; relatively early flowering response and good flower production; good branching and vigorous growth habit; good chlorophyll qualities for transportation; good temperature tolerance; medium leaf zonation.

1 Drawing Figure

The present invention comprises a new and distinct cultivar of geranium, botanically known as *Pelargonium zonale,* and hereinafter referred to by the cultivar name Casino.

Casino is a product of a planned breeding program which had the objective of creating new geranium cultivars having a dark salmon flower color, vigorous growth, good chlorophyll qualities for better transportation, good rooting and better temperature tolerance.

Casino was originated from a hybridization made by Ingeborg Schumann in a controlled breeding program in Hillscheid, Federal Republic of Germany in 1981. The female parent was Loripen. The male parent of Casino was Rheingauperle. Both parents are unpatended.

Casino was discovered and selected as one flowering plant within the progeny of the stated cross by Ingeborg Schumann on July of 1982 in a controlled environment in Hillscheid, Federal Republic of Germany.

The first act of asexual reproduction of Casino was accomplished when vegatative cuttings were taken from the initial selection in January of 1983 in a controlled environment in Hillscheid, Federal Republic of Germany by a technician working under formulations established and supervised by Ingeborg Schumann. Horticultural examination of selected units initiated in the spring of 1983 and 1984 has demonstrated that the combination of characteristics as herein disclosed for Casino are firmly fixed and are retained through successive generations of asexual reproduction.

Casino has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Casino, which in combination distinguish this geranium as a new and distinct cultivar.

1. Dark salmon flower color on top surface of petals, with the petals being white on the undersurface; a very distinct color arrangement.
2. Semi-double flower form.
3. Good branching and vigorous growth habit.

4. Good rooting.
5. Good chlorophyll quality for transporation.
6. Excellent temperature tolerance.
7. Medium leaf zonation.
8. Relatively early flowering response and good flower production.

Of the many commercial cultivars known to the present inventor, the most similar in comparison to Casino is Salmon Irene. Reference is made to the attached Chart A which compares certain characteristics of Casino to those same characteristics of Salmon Irene. In comparison to Salmon Irene, Casino has a darker salmon color with white buds, good chlorophyll quality, and better branching and rooting.

The accompanying photographic drawing shows typical flower and foliage characteristics of Casino, with colors being as true as possible with illustrations of this type.

In the following description color references are made to The Royal Horticultural Society Colour Chart. The color values were determined between 9:00 a.m. and 10:00 a.m. on May 20, 1985 under 30,000 Lux light intensity at Hillscheid, Federal Republic of Germany.

Classification:

*Botanical.*—A hybrid of the genus Pelargonium l'hert and species *Pelargonium zonale.*

*Commercial.*—Casino.

INFLORESCENCE

A. Umbel:

*Average diameter.*—127 mm.

*Average depth.*—81 mm.

*Penducle length.*—193 mm.

*Pedicel length.*—31 mm.

B. Corolla:

*Average diameter.*—50 mm.

*Form.*—Semi-double.

*Color (general tonality from a distance of three meters).*—Dark salmon. Upper Surface: 43A; white 155D under surface of petal.

C. Bud:

*Shape.*—Oval.

*Color.*—White to light rose.

D. Reproductive organs:

*Androecium.*—5–8 stamens.

*Gynoecium.*—5 lobed stigma.

E. Spring flowering response period: In Hillscheid, Federal Republic of Germany, in 1982, 55% of plants opened with at least one flower 13 weeks after planting of unrooted cuttings.

F. Outdoor flower production: The total flower count in 1982 in Hillscheid, Federal Republic of Germany, was between 48 and 53 flowers per plant for the June through October observation period.

G. Durability: Good shatter and rain resistance.

PLANT

A. Foliage:

*Form.*—Kidney shaped.

*Margin.*—Generally round, wavy and crenate.

*Color.*—Top surface: Dark to medium green. Zonation: Brown.

*Tolerance of botrytis.*—Good.

B. General appearance and form:

*Internode length.*—34 mm.

*Branching pattern.*—An average of 3.5 branches produced.

*Height.*—310 mm.

CHART A

| CULTIVAR | BRANCHING HABIT | COLOR | EARLY FLOWER RESPONSE (% of plants in flower after 13 weeks) |
|---|---|---|---|
| Salmon Irene | 3.0 | RHS 44D | 50% |
| Casino | 3.5 | RHS 43A | 55% |

| CULTIVAR | ROOTING | CHLOROPHYLL QUALITY |
|---|---|---|
| Salmon Irene | Slow | Bad to medium |
| Casino | Fast to medium | Good to very good |

I claim:

1. A new and distinct cultivar of geranium named Casino, as described and illustrated, and particularly characterized by its dark salmon flower color with white under surface; semi-double flower form; relatively early flowering response and good flower production; good branching and vigorous growth habit; good chlorophyll qualities for transportation; good temperature tolerance; and medium leaf zonation.

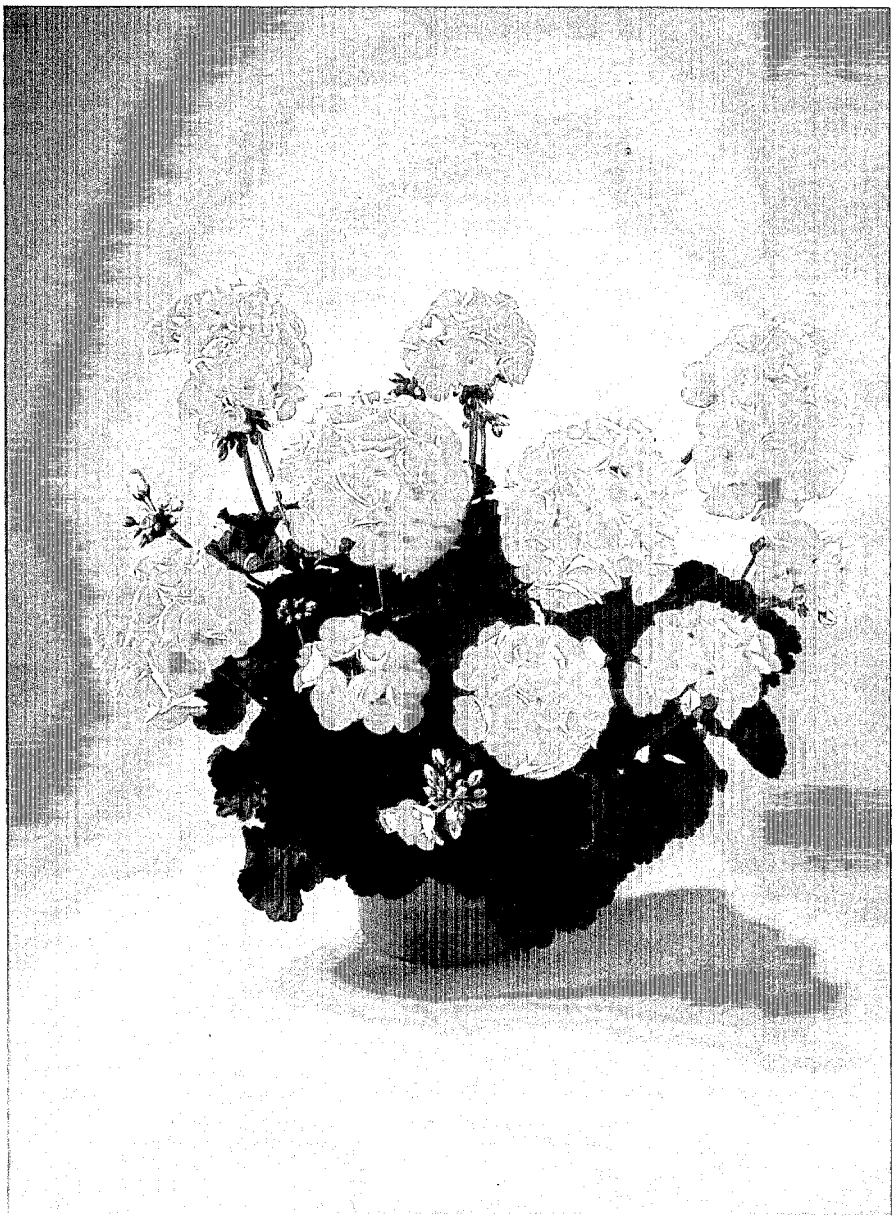

* * * * *